United States Patent [19]

Krause et al.

[11] Patent Number: 4,812,258
[45] Date of Patent: Mar. 14, 1989

[54] FLUORINE-CONTAINING PYRIMIDINE DERIVATIVES

[75] Inventors: Joachim Krause, Dieburg; Michael Römer, Rodgau; Ludwig Pohl, Darmstadt, all of Fed. Rep. of Germany; Bernhard Scheuble, Yokohama, Japan; Georg Weber, Erzhausen, Fed. Rep. of Germany

[73] Assignee: Merck Patent Gesellschaft Mit Beschränkter Haftung, Darmstadt, Fed. Rep. of Germany

[21] Appl. No.: 35,820

[22] Filed: Apr. 8, 1987

Related U.S. Application Data

[63] Continuation-in-part of Ser. No. 604,679, Apr. 27, 1984, abandoned.

[30] Foreign Application Priority Data

Apr. 27, 1983 [DE] Fed. Rep. of Germany ....... 3315295

[51] Int. Cl.[4] .................. G02F 1/13; C07D 239/26; C09K 19/34
[52] U.S. Cl. .......................... 252/299.61; 252/299.5; 350/350 R; 350/350 S; 544/242; 544/298; 544/315; 544/316; 544/318; 544/334; 544/335
[58] Field of Search ............... 350/350 R, 350 S; 544/334, 242, 298, 315, 316, 318, 335; 252/299.61, 299.63, 299.5, 299.6

[56] References Cited

U.S. PATENT DOCUMENTS

| | | | |
|---|---|---|---|
| 3,997,536 | 12/1976 | Boller et al. | 252/299.61 |
| 4,062,798 | 12/1977 | Boller et al. | 252/299.61 |
| 4,273,929 | 6/1981 | Boller et al. | 252/299.61 |
| 4,302,352 | 11/1981 | Eidenschimk et al. | 252/299.63 |
| 4,309,539 | 1/1982 | Boller et al. | 252/299.61 |
| 4,358,393 | 11/1982 | Zaschke et al. | 252/299.61 |
| 4,402,849 | 9/1980 | Krause et al. | 252/299.62 |
| 4,405,488 | 9/1983 | Sugimori et al. | 252/299.63 |
| 4,415,470 | 11/1983 | Eidenschimk et al. | 252/299.63 |
| 4,438,268 | 3/1984 | Zaschke et al. | 252/299.61 |
| 4,490,305 | 12/1984 | Eidenschimk et al. | 252/299.63 |
| 4,493,726 | 1/1985 | Burdeska et al. | 544/334 |
| 4,510,069 | 4/1985 | Eidenschimk et al. | 252/299.61 |
| 4,512,636 | 4/1985 | Andrews et al. | 252/299.61 |
| 4,533,488 | 8/1985 | Fukui et al. | 252/299.61 |
| 4,536,321 | 8/1985 | Sigimori et al. | 252/299.63 |
| 4,551,264 | 11/1985 | Eidenschimk et al. | 252/299.61 |
| 4,564,694 | 1/1986 | Hirai et al. | 252/299.61 |
| 4,621,901 | 11/1986 | Petrzilka et al. | 252/299.61 |
| 4,640,795 | 2/1987 | Ogawa et al. | 252/299.61 |
| 4,684,476 | 8/1987 | Kitano et al. | 252/299.61 |
| 4,713,197 | 12/1987 | Eidenschimk et al. | 252/299.61 |

FOREIGN PATENT DOCUMENTS

| | | | |
|---|---|---|---|
| 84194 | 7/1983 | European Pat. Off. | 252/299.61 |
| 123907 | 11/1984 | European Pat. Off. | 252/299.61 |
| 2257588 | 6/1973 | Fed. Rep. of Germany | 252/299.61 |
| 3315295 | 10/1984 | Fed. Rep. of Germany | 252/299.61 |
| 3404117 | 8/1985 | Fed. Rep. of Germany | 252/299.61 |
| 3500897 | 7/1986 | Fed. Rep. of Germany | 252/299.61 |
| 3606787 | 9/1987 | Fed. Rep. of Germany | 252/299.61 |
| 159505X | 3/1983 | German Democratic Rep. | 252/299.61 |
| 56-150030 | 11/1981 | Japan | 252/299.66 |
| 59-216876 | 12/1984 | Japan | 252/299.61 |
| 60-51778 | 3/1985 | Japan | 252/299.61 |
| 60-54371 | 3/1985 | Japan | 252/299.61 |
| 62-169765 | 7/1987 | Japan | 252/299.61 |
| 62-223171 | 10/1987 | Japan | 252/299.61 |
| 8600067 | 1/1986 | PCT Int'l Appl. | 252/299.61 |
| 2092169 | 8/1982 | United Kingdom | 252/299.61 |

OTHER PUBLICATIONS

Osman, M. et al., Z. Naturfdorsch, B: Anorgan Chem., Org. Chem., 38B(10), pp. 1221-6 (1983).
C.A., vol. 82, 16274w (1975).
C.A., vol. 94, 29954r (1981).
C.A., vol. 87, 5900 (1977).
Kane, S., et al., Heterocycles, vol. 19, No. 6, pp. 1079-1082 (1982).
Boller, A., et al., Mol. Cryst. Liq. Cryst., vol. 42, No. 1-3, pp. 215-231 (1977).
C.A., vol. 90, 121532s (1979).
C.A., vol. 83, 58747d (1975).

Primary Examiner—Teddy S. Gron
Attorney, Agent, or Firm—Millen & White

[57] ABSTRACT

Liquid crystalline fluorine-containing pyrimidine compounds have the formula I

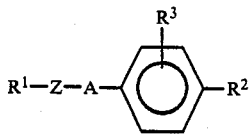

wherein $R^1$ and $R^2$ are H, R, OR or OCOR, and one of them can also be CN or F, or, if A is a covalent bond, also one or both of $R^1$ and $R^2$ can be 4-$R^4$-phenyl or 4-R-cyclohexyl, wherein $R^4$ is R, OR, cyano, f or OCOR; wherein R is an alkyl group of 1 to 12 C atoms; $R^3$ is F or, if one of the radicals $R^1$ or $R^2$ is F or 4-fluorophenyl, also H; Z is 1,3-pyrimidin-2,5-diyl; and A is 1,4-phenylene, 1,4-cyclohexylene or a covalent bond.

Fluorine-containing pyrimidine compounds are useful components of liquid crystal dielectrics for electro-optical display devices.

14 Claims, No Drawings

FLUORINE-CONTAINING PYRIMIDINE DERIVATIVES

CROSS-REFERENCE TO RELATED APPLICATION

This application is a CIP of 604,679, filed Apr. 27, 1984, now abandoned which is entirely incorporated by reference herein.

This invention relates to new fluorine-containing pyrimidine derivatives which are useful as components of liquid crystal dielectrics, and new liquid crystal dielectrics with at least one fluorine-containing pyrimidine derivative, which are suitable for use in electrooptical display devices, in particular those for multiplex operation.

SUMMARY OF THE INVENTION

It is an object of this invention to provide new stable liquid crystal or mesogenic compounds which are suitable as components of liquid crystal dielectrics.

Upon further study of the specification and appended claims, further objects and advantages of this invention will become apparent to those skilled in the art.

These objects have been achieved by providing fluorine-containing pyrimidine derivatives of the formula I

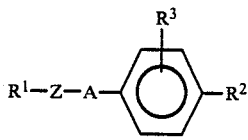

wherein $R^1$ and $R^2$ are H, R, OR or OCOR, and one of them can also be CN or F, or, if A is a covalent bond, also one or both of $R^1$ and $R^2$ can be 4-$R^4$-phenyl or 4-R-cyclohexyl, wherein $R^4$ is R, OR, cyano, F or OCOR; wherein R is an alkyl group of 1 to 12 C atoms; $R^3$ is F or, if one of the radicals $R^1$ or $R^2$ is F or 4-fluorophenyl, also H; Z is 1,3-pyrimidin-2,5-diyl; and A is 1,4-phenylene, 1,4-cyclohexylene or a covalent bond.

These are outstandingly suitable for the preparation of liquid crystal mixtures with a reduced tendency to form smectic phases at low temperatures, and have low $k_{33}/k_{11}$ quotients ($k_{33}$=elastic bending constant, $k_{11}$=elastic spreading constant; the slope of the characteristic line of the multiplexible mixture, inter alia, depends on the quotient $k_{33}/k_{11}$). These compounds have a wide field of application: depending on the choice of substituents, they can be used as base materials of which liquid crystal dielectrics predominantly consist, but liquid crystal base materials from other classes of compounds can also be added to the compounds of the formula I in order thus to prepare dielectrics with an extended liquid crystal mesophase or to influence the level of dielectric anisotropy of such a dielectric. "Low" $k_{33}/k_{11}$ values generally are 0.4–1.

DETAILED DISCUSSION

The compounds of the formula I are colorless in the pure state and form low-viscosity nematic mesophases in a wide temperature range favorably located for electrooptical use. They are very stable to chemicals, heat and light.

The invention thus relates to the compounds of the formula I and to a process for their preparation, characterized in that (a) a halogenopyrimidine of the formula II

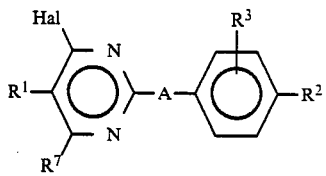

wherein $R^7$ is H or Hal and Hal is Cl or Br, and $R^1$, $R^2$, $R^3$ and A have the meaning given, is reduced, or in that (b) a compound which corresponds to the formula I but contains one or more amino groups instead of one or more fluorine atoms is diazotized, the diazotization product is converted into the corresponding diazonium tetrafluoroborate and this is decomposed by means of heat.

The invention furthermore relates to the use of the compounds of the formula I as components of liquid crystal dielectrics for electrooptical display elements, liquid crystal dielectrics for electrooptical display elements containing at least one compound of the formula I, and electrooptical display elements containing such dielectrics.

The fluorine-containing pyrimidine derivatives of the formula I according to the invention include, in particular, the preferred compounds of the following formulae Ia to Iq

| | |
|---|---|
| $R^1$—Z—Ph—F | (Ia) |
| $R^1$—Z—PhF—$R^2$ | (Ib) |
| $R^1$—Z—Ph—Ph—F | (Ic) |
| $R^4$—Ph—Z—Ph$R^3$—$R^2$ | (Id) |
| F—Z—Ph—$R^2$ | (Ie) |
| $R^1$—Z—Ph—PhF—$R^2$ | (If) |
| F—Ph—Z—Ph—Ph—$R^4$ | (Ig) |
| F—Z—Ph—Ph—$R^2$ | (Ih) |
| $R^1$—Z—Cy—Ph—F | (Ii) |
| $R^1$—Z—Cy—PhF—$R^2$ | (Ij) |
| $R^1$—Z—PhF—Cy—R | (Ik) |
| F—Z—Ph—Cy—R | (Il) |
| F—Z—Cy—Ph—$R^2$ | (Im) |
| R—Cy—Z—Ph—F | (In) |
| R—Cy—Z—PhF—$R^2$ | (Io) |
| $R^1$—Z—Ph$R^3$—Cy—R | (Ip) |
| $R^1$—Z—Ph$R^3$—Ph—$R^4$ | (Iq) | wherein Ph is 1,4-phenylene, PhF is 2- or 3-fluoro-1,4-phenylene, Cy is 1,4-cyclohexylene and $R^1$, $R^2$, $R^3$ and Z have the meaning given for formula I.

In the compounds of the formulae Ia to Iq above, those of formulae Ia, Ic, Ie, Ig–In and Ip, in particular Ia, Ij, In and Ip, are preferred.

In the compounds of the formula I above and below which contain a 1,4-cyclohexylene group, those which contain a trans-1,4-cyclohexylene group are preferred.

In the compounds of the formula I, the radicals $R^1$ and $R^2$ can be H, R, OR or OCOR, and one of them can also be CN or F, wherein the alkyl radical R can preferably be straight-chain, but can also be branched, and is preferably methyl, ethyl, n-propyl, n-butyl, n-pentyl, n-hexyl, n-heptyl, n-octyl, n-nonyl, n-decyl, n-undecyl or n-dodecyl.

In preferred compounds of formula I one of the radicals $R^1$ and $R^2$ is alkyl and the other CN or F, in particular CN.

Compounds of the formula I with a branched end group $R^1$ or $R^2$ are sometimes of importance because of their better solubility in the customary liquid crystal base materials, but in particular as chiral doping substances, if they possess optical activity as a result of the chain branching. Such branched end groups preferably contain not more than one chain branching. Preferred branched hydrocarbon radicals are those in which a methyl or ethyl group is present in the 1-, 2- or 3-position on a longer carbon chain, for example 2-methylpropyl, 2-methylbutyl, 3-methylbutyl, 2-methylpentyl, 3-methylpentyl, 2-ethylhexyl or 1-methylhexyl.

Preferred compounds of the formula I are those in which $R^1$ and $R^2$ together contain 3 to 14, in particular 4 to 12, carbon atoms. Compounds of the formula I in which the radicals $R^1$ and/or $R^2$ contain alkyl groups R with 2 to 8, in particular 3 to 6, carbon atoms are preferred. Compounds of the formula I in which one of the radicals $R^1$ or $R^2$ is 4-R-phneyl, 4-RO-phenyl, 4-cyanophenyl, 4-fluorophenyl or trans-4-R-cyclohexyl, in particular 4-cyanophenyl or 4-fluorophenyl, are also preferred.

The preferred compounds of part formula Ia include those of part formulae Iaa and Iab:

| | |
|---|---|
| R—Z—Ph—F | (Iaa) |
| RO—Z—Ph—F | (Iab) |

The preferred compounds of part formula Ib include those of part formulae Iba to Ibh:

| | |
|---|---|
| R—Z—PhF—R | (Iba) |
| R—Z—PhF—OR | (Ibb) |
| R—Z—PhF—CN | (Ibc) |
| R—Z—PhF—F | (Ibd) |
| R—Z—PhF—OCOR | (Ibe) |
| NC—Z—PhF—R | (Ibf) |
| NC—Z—PhF—OR | (Ibg) |
| NC—Z—PhF—OCOR | (Ibh) |

Among these, those of the part formulae Ibc, Ibd, Ibf, Ibg and Ibh are particularly preferred.

The preferred compounds of part formula Ic include those of part formulae Ica and Icb:

| | |
|---|---|
| R—Z—Ph—Ph—F | (Ica) |
| RO—Z—Ph—Ph—F | (Icb) |

The preferred compounds of part formula Id include those of part formulae Ida to Idr:

| | |
|---|---|
| R—Ph—Z—PhF—R | (Ida) |
| R—Ph—Z—PhF—OR | (Idb) |
| R—Ph—Z—PhF—OCOR | (Idc) |
| RO—Ph—Z—PhF—R | (Idd) |
| RO—Ph—Z—PhF—OR | (Ide) |
| RO—Ph—Z—PhF—OCOR | (Idf) |
| RCOO—Ph—Z—PhF—R | (Idg) |
| RCOO—Ph—Z—PhF—OR | (Idh) |
| RCOO—Ph—Z—PhF—OCOR | (Idi) |
| R—Ph—Z—PhF—CN | (Idj) |
| RO—Ph—Z—PhF—CN | (Idk) |
| RCOO—Ph—Z—PhF—CN | (Idl) |
| R—Ph—Z—Ph—F | (Idm) |
| RO—Ph—Z—Ph—F | (Idn) |
| RCOO—Ph—Z—Ph—F | (Ido) |
| F—Ph—Z—Ph—R | (Idp) |
| F—Ph—Z—Ph—OR | (Idq) |
| F—Ph—Z—Ph—OCOR | (Idr) |

Among these, those of part formulae Idj to Idr are particularly preferred.

The preferred compounds of part formulae Ie include those of part formulae Iea to Iec:

| | |
|---|---|
| F—Z—Ph—R | (Iea) |
| F—Z—Ph—OR | (Ieb) |
| F—Z—Ph—OCOR | (Iec) |

The preferred compounds of part formula If include those of part formulae Ifa to Ifh:

| | |
|---|---|
| R—Z—Ph—PhF—R | (Ifa) |
| R—Z—Ph—PhF—OR | (Ifb) |
| R—Z—Ph—PhF—OCOR | (Ifc) |
| R—Z—Ph—PhF—CN | (Ifd) |
| R—Z—Ph—PhF—F | (Ife) |
| NC—Z—Ph—PhF—R | (Iff) |
| NC—Z—Ph—PhF—OR | (Ifg) |
| NC—Z—Ph—PhF—OCOR | (Ifh) |

Among these, those of the part formulae Ifd to Ifh are particularly preferred.

The preferred compounds of part formula Ig include those of part formulae Iga to Igc:

F—Ph—Z—Ph—Ph—R (Iga)

F—Ph—Z—Ph—Ph—OR (Igb)

F—Ph—Z—Ph—Ph—OCOR (Igc)

The preferred compounds of part formula Ih include those of part formulae Iha to Ihc:

F—Z—Ph—Ph—R (Iha)

F—Z—Ph—Ph—OR (Ihb)

F—Z—Ph—Ph—OCOR (Ihc)

The preferred compounds of part formula Ii include those of part formulae Iia to Iib:

R—Z—Cy—Ph—F (Iia)

RO—Z—Cy—Ph—F (Iib)

The preferred compounds of part formula Ij include those of part formulae Ija to Ijh:

R—Z—Cy—PhF—R (Ija)

R—Z—Cy—PhF—OR (Ijb)

R—Z—Cy—PhF—OCOR (Ijc)

R—Z—Cy—PhF—CN (Ijd)

R—Z—Cy—PhF—F (Ije)

NC—Z—Cy—PhF—R (Ijf)

NC—Z—Cy—PhF—OR (Ijg)

NC—Z—Cy—PhF—OCOR (Ijh)

The preferred compounds of part formula Io include those of part formulae Ioa to Ioe:

R—Cy—Z—PhF—R (Ioa)

R—Cy—Z—PhF—OR (Iob)

R—Cy—Z—PhF—OCOR (Ioc)

R—Cy—Z—PhF—F (Iod)

R—Cy—Z—PhF—CN (Ioe)

Among these, those of part formulae Iod and Ioe are particularly preferred.

The preferred compounds of part formula Ip include those of part formulae Ipa to Ipd:

R—Z—PhF—Cy—R (Ipa)

F—Z—Ph—Cy—R (Ipb)

F—Z—PhF—Cy—R (Ipc)

NC—Z—PhF—Cy—R (Ipd)

Among these, those of the part formulae Ipa and Ipd are particularly preferred.

The preferred compounds of part formula Iq include those of part formulae Iqa to Iqh:

R—Z—PhF—Ph—R (Iqa)

R—Z—PhF—Ph—OR (Iqb)

R—Z—PhF—Ph—OCOR (Iqc)

R—Z—PhF—Ph—CN (Iqd)

R—Z—PhF—Ph—F (Iqe)

NC—Z—PhF—Ph—R (Iqf)

NC—Z—PhF—Ph—OR (Iqg)

NC—Z—PhF—Ph—OCOR (Iqh)

Among these, those of part formulae Iqd to Igh are particularly preferred.

The compounds of the formula I are preferably prepared by reductive dehalogenation of the compounds of the formula II. Compounds of the formula II are preferably prepared by condensation of an amidine of the formula III

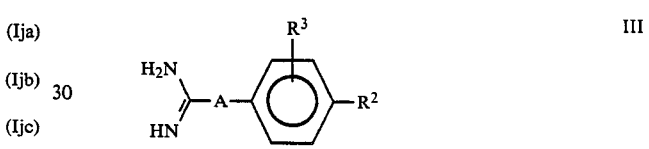

III wherein $R^2$, $R^3$ and A have the meaning given, or of one of its functional derivatives, with a malonic acid derivative of the formula IV, a formylacetic acid derivative of the formula V, a cyanoacetic acid derivative of the formula VI or a malonic acid dinitrile of the formula VII $R^1$—CH(COOR)$_2$    IV $R^1$—CH(CHO)(COOR)    V $R^1$—CH(CN)(COOR)    VI $R^1$—CH(CN)$_2$    VII wherein the radicals $R^1$ and R in each case have the meaning given, if appropriate, hydrolysis, and subsequent halogenation.

The reductive dehalogenation of the compounds of the formula II is carried out by methods which are known per se, for example preferably with hydrogen in the presence of a catalyst in the presence of an inert solvent at temperatures between −80° and +50°, preferably between −20° and +30°, under pressures between 1 and 2 bar. Suitable catalysts are most of the customary hydrogenation catalysts, preferably palladium-on-charcoal or Raney nickel. In principle, all the solvents usual for such hydrogenations can be employed as the solvent. Particularly suitable solvents are hydrocarbons, preferably benzene, toluene or xylenes, and alcohols, preferably methanol, ethanol, isopropanol or n-propanol. The reaction is preferably carried out in the presence of a base, preferably an organic amine, such as, for example, triethylamine.

The compounds of the formula I are furthermore obtainable by diazotization of corresponding amines and subsequent replacement of the diazonium groups by F atoms, for example by the Schiemann method.

The diazotization reaction to give the diazonium tetrafluoborate and thermal decomposition (Schiemann-Balz synthesis) can be carried out in a manner which is known per se, for example in accordance with one of the process variants described in "Organic Reactions", Volume 5 (1949), pages 193–228.

The starting substances can be obtained, for example, by nitration of corresponding pyrimidine derivatives which correspond to the formula I but contain hydrogen atoms instead of one or more F atoms; the resulting nitro compounds can then be reduced to the amino compounds, for example with tin and hydrochloric acid or by catalytic hydrogenation.

Some of the starting compounds of the formulae II to VII used in the syntheses described are known, and they can all be prepared analogously to the known starting compounds by standard processes of preparative organic chemistry in a manner which is customary per se.

The dielectrics according to the invention comprise 2 to 15, preferably 3 to 12, components, at least one of which is a compound of the formula I. The other constituents are preferably chosen from the nematic or nematogenic substances, in particular the known substances from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexyl-pyrimidines, phenyl- or cyclohexyl-dioxanes, optionally halogenated stilbenes, benzyl phenyl ethers, tolanes and substituted cinnamic acids.

The most important compounds which can be used as constituents of such liquid crystal dielectrics are characterized by the formula VIII

$R^6$—$E^1$—G—$E^2$—$R^5$     (VIII)

wherein $E^1$ and $E^2$ are each a carbocyclic or heterocyclic ring system from the group comprising 1,4-disubstituted benzene and cyclohexane rings, 4,4'-disubstituted biphenyl, phenylcyclohexane and cyclohexyl-cyclohexane systems, 2,5-disubstituted pyrimidine and 1,3-dioxane rings, 2,6-disubstituted naphthalene, di- and tetra-hydronaphthalene, quinazoline and tetrahydroquinazoline, G is

| G | —CH=CH— | —N(O)=N— |
|---|---|---|
| | —CH=CY— | —CH=N(O)— |
| | —C≡C— | —CH$_2$—CH$_2$— |
| | —CO—O— | —CH$_2$—O— |
| | —CO—S— | —CH$_2$—S— |
| | —CH=N— | —COO—Phe—COO— | or a C—C single bond, y is halogen, preferably chlorine, or —CN and $R^6$ and $R^5$ are alkyl, alkoxy, alkanoyloxy or alkoxycarbonyloxy with up to 18, preferably up to 8, carbon atoms, or one of these radicals is also CN, NC, NO$_2$, CF$_3$, F, Cl or Br.

In most of these compounds, $R^6$ and $R^5$ differ from one another, one of these radicals usually being an alkyl or alkoxy group. However, other variants of the substituents envisaged are also useful. The 1,4-disubstituted benzene rings in these compounds can also be substituted laterally by F or CN. Many such substances or mixtures thereof are commercially available, and all these substances can be prepared by methods which are known from the literature.

The dielectrics according to the invention contain about 0.1 to 100, preferably 10 to 100%, of compounds of the formula I, at least two compounds of the formula I being present if other compounds are absent.

The dielectrics according to the invention are prepared in a manner which is customary per se. As a rule, the components are dissolved in one another, preferably at elevated temperature.

The liquid crystal dielectrics according to the invention can be modified by suitable additives such that they can be used in all the types of liquid crystal display elements hitherto disclosed.

Such additives are known to the expert and are described in detail in the literature. For example, conductive salts, preferably ethyl-dimethyl-dodecylammonium 4-hexyloxybenzoate, tetrabutylammonium tetraphenylboranate or complex salts of crown esters (compare, for example, B. I. Haller et al., Mol.Cryst.Liq.Cryst. Volume 24, pages 249–258 (1973)) can be added to improve the conductivity, dichroic dyestuffs can be added to produce colo guest-host systems or substances can be added to modify the dielectric anisotropy, the viscosity and/or the orientation of the nematic phases. Substances of this type are described, for example, in German Offenlegungsschriften Nos. 2,209,127, 2,240,864, 2,321,632, 2,338,281, 2,450,088, 2,637,430, 2,853,728 and 2,902,177.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding text, all temperatures are set forth uncorrected in degrees Celsius and all parts and percentages are by weight, unless otherwise indicated.

In the examples, m.p. is the melting point and c.p. is the clear point of a liquid crystal substance.

EXAMPLE 1

53 g of 2-p-fluorophenyl-b 4,6-dichloro-5-n-hexylpyrimidine (obtainable by reaction of p-fluorobenzonitrile with ethanol/HCl to give p-fluorobenzimidoethyl ester hydrochloride, reaction with ethanolic NH$_3$ to give p-fluorobenzamidine hydrochloride, reaction with diethyl n-hexylmalonate to give 2-p-fluorophenyl-4,6-dihydroxy-5-n-hexylpyrimidine and heating with POCl$_3$/dimethylaniline) is dissolved in 750 ml of ethanol and 75 ml of triethylamine and the solution is hydrogenated on 25 g of 5% Pd-on-C at 20° under 1 bar until somewhat more than the calculated amount of hydrogen has been taken up. The mixture is filtered, the filtrate is evaporated and the residue is purified by dissolving in methylene chloride, washing the solution with water, dilute hydrochloric acid and again with water and evaporating again to give 2-p-fluorophenyl-5-n-hexylpyrimidine, m.p. 39° (from ethanol).

The following compounds are prepared analogously:
2-p-fluorophenyl-5-methylpyrimidine
2-p-fluorophenyl-5-ethylpyrimidine
2-p-fluorophenyl-5-n-propylpyrimidine
2-p-fluorophenyl-5-n-butylpyrimidine
2-p-fluorophenyl-5-n-pentylpyrimidine
2-p-fluorophenyl-5-n-heptylpyrimidine
2-p-fluorophenyl-5-n-octylpyrimidine
2-p-fluorophenyl-5-n-nonylpyrimidine, m.p. 23.5°
2-p-fluorophenyl-5-n-decylpyrimidine
2-p-fluorophenyl-5-n-undecylpyrimidine and
2-p-fluorophenyl-5-n-dodecylpyrimidine.

EXAMPLE 2

8.8 g of 2-(3-amino-4-n-dodecyloxyphenyl)-5-n-hexylpyrimidine (m.p. 57.5°, obtainable by reaction of 2-(4-n-dodecyloxyphenyl)-5-n-hexylpyrmidine with nitric acid to give 2-(3-nitro-4-n-dodecyloxyphenyl)-5-n-hexylpyrimidine and subsequent reduction with $H_2$/Raney nickel) is dissolved in 25 ml of dioxane at 50° and 25 ml of 35% tetrafluoboric acid is added dropwise, with stirring. After one hour, the resulting emulsion is cooled to 0°, whereupon crystallization occurs. A solution of 2.4 g of sodium nitrite in 25 ml of water is added to the suspension and the mixture is stirred for one hour. The resulting diazonium tetrafluoroborate is filtered off with suction, washed with ice-water and dried. 5 g of the diazonium salt is heated at 200° until the evolution of gas has ended. 2-(3-Fluoro-4-n-dodecyloxyphenyl)-5-n-hexylpyrimidine of m.p. 51.5° and c.p. 44° is obtained by purification by chromatography.

The following compounds are prepared analogously:
2-(3-fluoro-4-(trans-4-n-butylcyclohexyl)phenyl)-5-n-butylpyrimidine
2-(3-fluoro-4-(trans-4-n-butylcyclohexyl)phenyl)-5-n-pentylpyrimidine
2-(3-fluoro-4-(trans-4-n-butylcyclohexyl)phenyl)-5-n-hexylpyrimidine
2-(3-fluoro-4-(trans-4-n-butylcyclohexyl)phenyl)-5-n-heptylpyrimidine
2-(3-fluoro-4-(trans-4-n-butylcyclohexyl)phenyl)-5-n-octylpyrimidine
2-(3-fluoro-4-(trans-4-n-pentylcyclohexyl)phenyl)-5-n-butylpyrimidine
2-(3-fluoro-4-(trans-4-n-pentylcyclohexyl)phenyl)-5-n-pentylpyrimidine
2-(3-fluoro-4-(trans-4-n-pentylcyclohexyl)phenyl)-5-n-hexylpyrimidine
2-(3-fluoro-4-(trans-4-n-pentylcyclohexyl)phenyl)-5-n-heptylpyrimidine
2-(3-fluoro-4-(trans-4-n-pentylcyclohexyl)phenyl)-5-n-octylpyrimidine
2-(3-fluoro-4-(trans-4-n-hexylcyclohexyl)phenyl)-5-n-butylpyrimidine
2-(3-fluoro-4-(trans-4-n-hexylcyclohexyl)phenyl)-5-n-pentylpyrimidine
2-(3-fluoro-4-(trans-4-n-hexylcyclohexyl)phenyl)-5-n-hexylpyrimidine
2-(3-fluoro-4-(trans-4-n-hexylcyclohexyl)phenyl)-5-n-heptylpyrimidine
2-(3-fluoro-4-(trans-4-n-hexylcyclohexyl)phenyl)-5-n-octylpyrimidine
2-(3-fluoro-4-(trans-4-n-heptylcyclohexyl)phenyl)-5-n-butylpyrimidine
2-(3-fluoro-4-(trans-4-n-heptylcyclohexyl)phenyl)-5-n-pentylpyrimidine
2-(3-fluoro-4-(trans-4-n-heptylcyclohexyl)phenyl)-5-n-hexylpyrimidine
2-(3-fluoro-4-(trans-4-n-heptylcyclohexyl)phenyl)-5-n-heptylpyrimidine
2-(3-fluoro-4-(trans-4-n-heptylcyclohexyl)phenyl)-5-n-octylpyrimidine
2-(3-fluoro-4-(trans-4-n-octylcyclohexyl)phenyl)-5-n-butylpyrimidine
2-(3-fluoro-4-(trans-4-n-octylcyclohexyl)phenyl)-5-n-pentylpyrimidine
2-(3-fluoro-4-(trans-4-n-octylcyclohexyl)phenyl)-5-n-hexylpyrimidine
2-(3-fluoro-4-(trans-4-n-octylcyclohexyl)phenyl)-5-n-heptylpyrimidine
2-(3-fluoro-4-(trans-4-n-octylcyclohexyl)phenyl)-5-n-octylpyrimidine
2-(3-fluoro-4-n-butylphenyl)-5-(4-n-butylphenyl)-pyrimidine
2-(3-fluoro-4-n-butylphenyl)-5-(4-n-pentylphenyl)-pyrimidine
2-(3-fluoro-4-n-butylphenyl)-5-(4-n-hexylphenyl)-pyrimidine
2-(3-fluoro-4-n-butylphenyl)-5-(4-n-heptylphenyl)-pyrimidine
2-(3-fluoro-4-n-butylphenyl)-5-(4-n-octylphenyl)-pyrimidine
2-(3-fluoro-4-n-pentylphenyl)-5-(4-n-butylphenyl)-pyrimidine
2-(3-fluoro-4-n-pentylphenyl)-5-(4-n-pentylphenyl)-pyrimidine
2-(3-fluoro-4-n-pentylphenyl)-5-(4-n-hexylphenyl)-pyrimidine
2-(3-fluoro-4-n-pentylphenyl)-5-(4-n-heptylphenyl)-pyrimidine
2-(3-fluoro-4-n-pentylphenyl)-5-(4-n-octylphenyl)-pyrimidine
2-(3-fluoro-4-n-hexylphenyl)-5-(4-n-butylphenyl)-pyrimidine
2-(3-fluoro-4-n-hexylphenyl)-5-(4-n-pentylphenyl)-pyrimidine
2-(3-fluoro-4-n-hexylphenyl)-5-(4-n-hexylphenyl)-pyrimidine
2-(3-fluoro-4-n-hexylphenyl)-5-(4-n-heptylphenyl)-pyrimidine
2-(3-fluoro-4-n-hexylphenyl)-5-(4-n-octylphenyl)-pyrimidine
2-(3-fluoro-4-n-heptylphenyl)-5-(4-n-butylphenyl)-pyrimidine
2-(3-fluoro-4-n-heptylphenyl)-5-(4-n-pentylphenyl)-pyrimidine
2-(3-fluoro-4-n-heptylphenyl)-5-(4-n-hexylphenyl)-pyrimidine
2-(3-fluoro-4-n-heptylphenyl)-5-(4-n-heptylphenyl)-pyrimidine
2-(3-fluoro-4-n-heptylphenyl)-5-(4-n-octylphenyl)-pyrimidine
2-(3-fluoro-4-n-octylphenyl)-5-(4-n-butylphenyl)-pyrimidine
2-(3-fluoro-4-n-octylphenyl)-5-(4-n-pentylphenyl)-pyrimidine 2-(3-fluoro-4-n-octylphenyl)-5-(4-n-hexylphenyl)-pyrimidine
2-(3-fluoro-4-n-octylphenyl)-5-(4-n-heptylphenyl)-pyrimidine
2-(3-fluoro-4-n-octylphenyl)-5-(4-n-octylphenyl)-pyrimidine
2-(3-fluoro-4-n-butoxyphenyl)-5-n-butylpyrimidine
2-(3-fluoro-4-n-butoxyphenyl)-5-n-pentylpyrimidine
2-(3-fluoro-4-n-butoxyphenyl)-5-n-hexylpyrimidine
2-(3-fluoro-4-n-butoxyphenyl)-5-n-heptylpyrimidine
2-(3-fluoro-4-n-butoxyphenyl)-5-n-octylpyrimidine
2-(3-fluoro-4-n-pentyloxyphenyl)-5-n-butylpyrimidine
2-(3-fluoro-4-n-pentyloxyphenyl)-5-n-pentylpyrimidine
2-(3-fluoro-4-n-pentyloxyphenyl)-5-n-hexylpyrimidine
2-(3-fluoro-4-n-pentyloxyphenyl)-5-n-heptylpyrimidine
2-(3-fluoro-4-n-pentyloxyphenyl)-5-n-octylpyrimidine
2-(3-fluoro-4-n-hexyloxyphenyl)-5-n-butylpyrimidine
2-(3-fluoro-4-n-hexyloxyphenyl)-5-n-pentylpyrimidine
2-(3-fluoro-4-n-hexyloxyphenyl)-5-n-hexylpyrimidine
2-(3-fluoro-4-n-hexyloxyphenyl)-5-n-heptylpyrimidine
2-(3-fluoro-4-n-hexyloxyphenyl)-5-n-octylpyrimidine
2-(3-fluoro-4-n-heptyloxyphenyl)-5-n-butylpyrimidine
2-(3-fluoro-4-n-heptyloxyphenyl)-5-n-pentylpyrimidine
2-(3-fluoro-4-n-heptyloxyphenyl)-5-n-hexylpyrimidine
2-(3-fluoro-4-n-heptyloxyphenyl)-5-n-heptylpyrimidine
2-(3-fluoro-4-n-heptyloxyphenyl)-5-n-octylpyrimidine
2-(3-fluoro-4-n-octyloxyphenyl)-5-n-butylpyrimidine
2-(3-fluoro-4-n-octyloxyphenyl)-5-n-pentylpyrimidine
2-(3-fluoro-4-n-octyloxyphenyl)-5-n-hexylpyrimidine
2-(3-fluoro-4-n-octyloxyphenyl)-5-n-heptylpyrimidine and
2-(3-fluoro-4-n-octyloxyphenyl)-5-n-octylpyrimidine.

EXAMPLE 3

56 g of 2-(3-amino-4-n-pentylphenyl)-5-n-hexylpyrimidine (m.p. 92°, obtainable by reaction of 2-(4-n-pentylphenyl)-5-n-hexylpyrimidine (c.p. 28.5°) with nitric acid to give 2-(3-nitro-4-n-pentylphenyl)-5-n-hexylpyrimidine (m.p. 41.5°) and hydrogenation on Raney nickel) is dissolved in 150 ml of dioxane at 50° and 208 ml of 35% tetrafluoroboric acid are added dropwise, with stirring. After one hour, the resulting emulsion is cooled to 0°, whereupon crystallization occurs. A solution of 20 g of sodium nitrite in 150 ml of water is added to the suspension and the mixture is stirred for one hour. The resulting mixture diazonium tetrafluoborate is filtered off with suction, washed with ice-water and dried. 5 g of the diazonium salt is heated at 200° until the evolution of gas has ended. 2-(3-Fluoro-4-n-pentylphenyl)-5-n-hexylpyrimidine of m.p. 30° is obtained by purification by chromatography.

The following compounds are prepared analogously:
2-(3-fluoro-4-n-butylphenyl)-5-(trans-4-n-butylcyclohexyl)pyrimidine
2-(3-fluoro-4-n-butylphenyl)-5-(trans-4-n-pentylcyclohexyl)pyrimidine
2-(3-fluoro-4-n-butylphenyl)-5-(trans-4-n-hexylcyclohexyl)pyrimidine
2-(3-fluoro-4-n-butylphenyl)-5-(trans-4-n-heptylcyclohexyl)pyrimidine
2-(3-fluoro-4-n-butylphenyl)-5-(trans-4-n-octylcyclohexyl)pyrimidine
2-(3-fluoro-4-n-pentylphenyl)-5-(trans-4-n-butylcyclohexyl)pyrimidine
2-(3-fluoro-4-n-pentylphenyl)-5-(trans-4-n-pentylcyclohexyl)pyrimidine
2-(3-fluoro-4-n-pentylphenyl)-5-(trans-4-n-hexylcyclohexyl)pyrimidine
2-(3-fluoro-4-n-pentylphenyl)-5-(trans-4-n-heptylcyclohexyl)pyrimidine
2-(3-fluoro-4-n-pentylphenyl)-5-(trans-4-n-octylcyclohexyl)pyrimidine
2-(3-fluoro-4-n-hexylphenyl)-5-(trans-4-n-butylcyclohexyl)pyrimidine
2-(3-fluoro-4-n-hexylphenyl)-5-(trans-4-n-pentylcyclohexyl)pyrimidine
2-(3-fluoro-4-n-hexylphenyl)-5-(trans-4-n-hexylcyclohexyl)primidine
2-(3-fluoro-4-n-hexylphenyl)-5-(trans-4-n-heptylcyclohexyl)pyrimidine
2-(3-fluoro-4-n-hexylphenyl)-5-(trans-4-n-octylcyclohexyl)pyrimidine
2-(3-fluoro-4-n-heptylphenyl)-5-(trans-4-n-butylcyclohexyl)pyrimidine
2-(3-fluoro-4-n-heptylphenyl)-5-(trans-4-n-pentylcyclohexyl)pyrimidine
2-(3-fluoro-4-n-heptylphenyl)-5-(trans-4-n-hexylcyclohexyl)pyrimidine
2-(3-fluoro-4-n-heptylphenyl)-5-(trans-4-n-heptylcyclohexyl)pyrimidine
2-(3-fluoro-4-n-heptylphenyl)-5-(trans-4-n-octylcyclohexyl)pyrimidine
2-(3-fluoro-4-n-octylphenyl)-5-(trans-4-n-butylcyclohexyl)pyrimidine
2-(3-fluoro-4-n-octylphenyl)-5-(trans-4-n-pentylcyclohexyl)pyrimidine
2-(3-fluoro-4-n-octylphenyl)-5-(trans-4-n-hexylcyclohexyl)pyrimidine
2-(3-fluoro-4n-octylphenyl)-5-(trans-4-n-heptylcyclohexyl)pyrimidine
2-(3-fluoro-4-n-octylphenyl)-5-(trans-4-n-octylcyclohexyl)pyrimidine
2-(3-fluoro-4-n-butylphenyl)-5-n-butylpyrimidine
2-(3-fluoro-4-n-butylphenyl)-5-n-pentylpyrimidine
2-(3-fluoro-4-n-butylphenyl)-5-n-hexylpyrimidine
2-(3-fluoro-4-n-butylphenyl)-5-n-heptylpyrimidine
2-(3-fluoro-4-n-butylphenyl)-5-n-octylpyrimidine
2-(3-fluoro-4-n-pentylphenyl)-5-n-butylpyrimidine
2-(3-fluoro-4-n-pentylphenyl)-5-n-pentylpyrimidine
2-(3-fluoro-4-n-pentylphenyl)-5-n-hexylpyrimidine
2-(3-fluoro-4-n-pentylphenyl)-5-n-heptylpyrimidine
2-(3-fluoro-4-n-pentylphenyl)-5-n-octylpyrimidine
2-(3-fluoro-4-n-hexylphenyl)-5-n-butylpyrimidine
2-(3-fluoro-4-n-hexylphenyl)-5-n-pentylpyrimidine
2-(3-fluoro-4-n-hexylphenyl)-5-n-hexylpyrimidine
2-(3-fluoro-4-n-hexylphenyl)-5-n-heptylpyrimidine
2-(3-fluoro-4-n-hexylphenyl)-5-n-octylpyrimidine
2-(3-fluoro-4-n-heptylphenyl)-5-n-butylpyrimidine
2-(3-fluoro-4-n-heptylphenyl)-5-n-pentylpyrimidine
2-(3-fluoro-4-n-heptylphenyl)-5-n-hexylpyrimidine
2-(3-fluoro-4-n-heptylphenyl)-5-n-heptylpyrimidine
2-(3-fluoro-4-n-heptylphenyl)-5-n-octylpyrimidine
2-(3-fluoro-4-n-octylphenyl)-5-n-butylpyrimidine
2-(3-fluoro-4-n-octylphenyl)-5-n-pentylpyrimidine
2-(3-fluoro-4-n-octylphenyl)-5-n-hexylpyrimidine
2-(3-fluoro-4-n-octylphenyl)-5-n-heptylpyrimidine
2-(3-fluoro-4-n-octylphenyl)-5-n-octylpyrimidine
2-cyano-5-(3-fluoro-4n-butylphenyl)-pyrimidine
2-cyano-5-(3-fluoro-4-n-pentylphenyl)-pyrimidine
2-cyano-5-(3-fluoro-4-n-hexylphenyl)-pyrimidine
2-cyano-5-(3-fluoro-4-n-heptylphenyl)-pyrimidine and
2-cyano-5-(3-fluoro-4-n-octylphenyl)-pyrimidine.

EXAMPLE 4

82.6 g of 2-(2'-fluoro-4'-n-pentylbiphenyl-4-yl)-4,6-dichloro-5-n-nonylpyrimidine m.p. 51°, obtainable by reaction of 4-n-pentyl-2-fluoro-4′-cyanobiphenyl, m.p. 54°, with ethanol/HCl and ethanolic NH₃ to give the corresponding amidine hydrochloride, reaction with diethyl n-nonyl malonate to give 2-(2′-fluoro-4′-n-pentylbiphenyl-4-yl)-4,6-dihydroxy-5-n-nonylpyrimidine and heating with POCl$_3$/dimethylaniline is dissolved in 750 ml of ethanol and 75 ml of triethylamine and the solution is hydrogenated and worked up analogously to Example 1. 2-(2′-fluoro-4′-n-pentylbiphenyl-4-yl)-5-n-nonylpyrimidine of m.p. 51°, S/N 81° and c.p. 131° is obtained.

The following compounds are prepared analogously:
2-(2′-fluoro-4′-n-butylbiphenyl-4-yl)-5-n-butylpyrimidine
2-(2′-fluoro-4′-n-butylbiphenyl-4-yl)-5-n-pentylpyrimidine
2-(2′-fluoro-4′-n-butylbiphenyl-4-yl)-5-n-hexylpyrimidine
2-(2′-fluoro-4′-n-butylbiphenyl-4-yl)-5-n-heptylpyrimidine
2-(2′-fluoro-4′-n-butylbiphenyl-4-yl)-5-n-octylpyrimidine
2-(2′-fluoro-4′-n-butylbiphenyl-4-yl)-5-n-nonylpyrimidine
2-(2′-fluoro-4′-n-pentylbiphenyl-4-yl)-5-n-butylpyrimidine
2-(2°-fluoro-4′-n-pentylbiphenyl-4-yl)-5-n-pentylpyrimidine
2-(2′-fluoro-4′-n-pentylbiphenyl-4-yl)-5-n-hexylpyrimidine
2-(2′-fluoro-4′-n-pentylbiphenyl-4-yl)-5-n-heptylpyrimidine
2-(2′-fluoro-4′-n-pentylbiphenyl-4-yl)-5-n-octylpyrimidine
2-(2′-fluoro-4′-n-pentylbiphenyl-4-yl)-5-n-decylpyrimidine
2-(2′-fluoro-4′-n-pentylbiphenyl-4-yl)-5-n-undecylpyrimidine
2-(2′-fluoro-4′-n-pentylbiphenyl-4-yl)-5-n-dodecylpyrimidine
2-(2′-fluoro-4′-n-hexylbiphenyl-4-yl)-5-n-butylpyrimidine
2-(2′-fluoro-4′-n-hexylbiphenyl-4-yl)-5-n-pentylpyrimidine
2-(2′-fluoro-4′-n-hexylbiphenyl-4-yl)-5-n-hexylpyrimidine
2-(2′-fluoro-4′-n-hexylbiphenyl-4-yl)-5-n-heptylpyrimidine
2-(2′-fluoro-4′-n-hexylbiphenyl-4-yl)-5-n-octylpyrimidine
2-(2′-fluoro-4′-n-hexylbiphenyl-4-yl)-5-n-nonylpyrimidine
2-(2′-fluoro-4′-n-heptylbiphenyl-4-yl)-5-n-butylpyrimidine
2-(2′-fluoro-4′-n-heptylbiphenyl-4-yl)-5-n-pentylpyrimidine
2-(2′-fluoro-4′-n-heptylbiphenyl-4-yl)-5-n-hexylpyrimidine
2-(2′-fluoro-4′-n-heptylbiphenyl-4-yl)-5-n-heptylopyrimidine
2-(2′-fluoro-4′-n-heptylbiphenyl-4-yl)-5-n-octylpyrimidine
2-(2′-fluoro-4′-n-octylbiphenyl-4-yl)-5-n-butylpyrimidine
2-(2′-fluoro-4′-n-octylbiphenyl-4-yl)-5-n-pentylpyrimidine
2-(2′-fluoro-4′-n-octylbiphenyl-4-yl)-5-n-hexylpyrimidine
2-(2′-fluoro-4′-n-octylbiphenyl-4-yl)-5-n-heptylpyrimidine
2-(2′-fluoro-4′-n-octylbiphenyl-4-yl)-5-n-octylpyrimidine
2-(2-fluorobiphenyl-4-yl)-5-n-butylpyrimidine
2-(2-fluorobiphenyl-4-yl)-5-n-pentylpyrimidine
2-(2-fluorobiphenyl-4-yl)-5-n-hexylpyrimidine
2-(2-fluorobiphenyl-4-yl)-5-n-heptylpyrimidine
2-(2-fluorobiphenyl-4-yl)-5-n-octylpyrimidine
2-(2-fluoro-4′-n-pentylbiphenyl-4-yl)-5-n-butylpyrimidine
2-(2-fluoro-4′-n-pentylbiphenyl-4-yl)-5-n-pentylpyrimidine
2-(2-fluoro-4′-n-pentylbiphenyl-4-yl)-5-n-hexylpyrimidine
2-(2-fluoro-4′-n-pentylbiphenyl-4-yl)-5-n-heptylpyrimidine
2-(2-fluoro-4′-n-pentylbiphenyl-4-yl)-5-n-octylpyrimidine
2-(2-fluoro-4′-n-hexylbiphenyl-4-yl)-5-n-butylpyrimidine
2-(2-fluoro-4′-n-hexylbiphenyl-4-yl)-5-n-pentylpyrimidine
2-(2-fluoro-4′-n-hexylbiphenyl-4-yl)-5-n-hexylpyrimidine
2-(2-fluoro-4′-n-hexylbiphenyl-4-yl)-5-n-heptylpyrimidine
2-(2-fluoro-4′-n-hexylbiphenyl-4-yl)-5-n-octylpyrimidine
2-(2-fluoro-4′-n-heptylbiphenyl-4-yl)-5-n-butylpyrimidine
2-(2-fluoro-4′-n-heptylbiphenyl-4-yl)-5-n-pentylpyrimidine
2-(2-fluoro-4′-n-heptylbiphenyl-4-yl)-5-n-hexylpyrimidine
2-(2-fluoro-4′-n-heptylbiphenyl-4-yl)-5-n-heptylpyrimidine and
2-(2-fluoro-4′-n-heptylbiphenyl-4-yl)-5-n-octylpyrimidine.

EXAMPLE 5

A mixture of 37.8 g of 2-(3-nitro-4-bromophenyl)-5-n-heptylpyrimidine (obtainable by nitration of 4-bromobenzonitrile, converting the 3-nitro-4-bromobenzonitrile into the corresponding amidine hydrochloride and heating the latter together with n-heptylmalondialdehydtetramethylacetale), 18 g of Cu-(I)-cyanide and 100 ml of 1,3-dimethyltetrahydro-2(1H)pyrimidinon (DMPU) is heated at 150° for 3 hours. After cooling the mixture is filtered, the filtrate and the residue are extracted with methylene chloride and the organic phase is evaporated. 2-(3-Nitro-4-cyanophenyl)-5-n-heptylpyrimidine (F. 73°) is obtained by purification by chromatography. The obtained material is heated together with 33.4 g of CsF in 120 ml of DMPU at 110° for 4 hours. After cooling the mixture is poured onto 600 ml of ice water. After extraction with methylene chloride and purification by chromatography 2-(3-fluoro-4-cyanophenyl)-5-n-heptylpyrimidine (m.p. 43°, clp. 0°, $\Delta\epsilon = -37$) is obtained The following compounds are prepared analogously:
2-(3-fluoro-4-cyanophenyl)-5-octylpyrimidine
2-(3-fluoro-4-cyanophenyl)-5-nonylpyrimidine
2-(3-fluoro-4-cyanophenyl)-5-decylpyrimidine
2-(3-fluoro-4-cyanophenyl)-5-hexylpyrimidine, m.p. 47°, clp. −10°
2-(3-fluoro-4-cyanophenyl)-5-pentylpyrimidine, m.p. 62°, clp. 0°

2-(3-fluoro-4-cyanophenyl)-5-butylpyrimidine
2-(3-fluoro-4-cyanophenyl)-5-propylpyrimidine, m.p. 87°, clp. +10°
2-(3-fluoro-4-cyanophenyl)-5-ethylpyrimidine
2-(3-fluoro-4-cyanophenyl)-5-(p-ethylphenyl)-pyrimidine
2-(3-fluoro-4-cyanophenyl)-5-(p-propylphenyl)-pyrimidine
2-(3-fluoro-4-cyanophenyl)-5-(p-butylphenyl)-pyrimidine
2-(3-fluoro-4-cyanophenyl)-5-(p-pentylphenyl)-pyrimidine
2-(3-fluoro-4-cyanophenyl)-5-(p-hexylphenyl)-pyrimidine
2-(3-fluoro-4-cyanophenyl)-5-(p-heptylphenyl)-pyrimidine
2-(3-fluoro-4-cyanophenyl)-5-(p-octylphenyl)-pyrimidine
2-(3-fluoro-4-cyanophenyl)-5-(p-nonylphenyl)-pyrimidine
2-(3-fluoro-4-cyanophenyl)-5-(p-decylphenyl)-pyrimidine
2-(3-fluoro-4-cyanophenyl)-5-(trans-4-ethylcyclohexyl)pyrimidine
2-(3-fluoro-4-cyanophenyl)-5-(trans-4-propylcyclohexyl)pyrimidine
2-(3-fluoro-4-cyanophenyl)-5-(trans-4-butylcyclohexyl)pyrimidine
2-(3-fluoro-4-cyanophenyl)-5-(trans-4-pentylcyclohexyl)pyrimidine
2-(3-fluoro-4-cyanophenyl)-5-(trans-4-hexylcyclohexyl)pyrimidine
2-(3-fluoro-4-cyanophenyl)-5-(trans-4-heptylcyclohexyl)pyrimidine
2-(3-fluoro-4-cyanophenyl)-5-(trans-4-octylcyclohexyl)pyrimidine
2-(3-fluoro-4-cyanophenyl)-5-(trans-4-nonylcyclohexyl)pyrimidine
2-(3-fluoro-4-cyanophenyl)-5-(trans-4-decylcyclohexyl)pyrimidine

EXAMPLE A

A liquid crystal mixture of
14.2% of 4-(trans-4-propylcyclohexyl)-benzonitrile
19.2% of 4-(trans-4-n-pentylcyclohexyl)-benzonitrile
13.3% of 4-(trans-4-n-propylcyclohexyl)-ethoxybenzene
10.0% of 4-(trans-4-n-propylcyclohexyl)-butoxybenzene
18.4% of 4-(trans-4-n-pentylcyclohexyl)-4'-ethylbiphenyl 8.3% of 4-(trans-4-n-pentylcyclohexyl)-4'-(trans-4-n-propylcyclohexyl)-biphenyl and
16.6% of 2-(4-n-pentylphenyl)-5-n-hexylpyrimidine
has a smectic/nematic phase transition at −12° and a clear point of 72°. By replacing the last component by the same amount of 2-(3-fluoro-4-n-pentylphenyl)1-5-n-hexylpyrimidine, a liquid crystal mixture is obtained which has a clear point of 65° and shows no smectic phase down to −20°.

EXAMPLE B

A liquid crystal mixture of
12.6% of 4-(trans-4-propylcyclohexyl)-benzonitrile
17.0% of 4-(trans-4-n-pentylcyclohexyl)-benzonitrile
11.8% of 4-(trans-4-n-propylcyclohexyl)-ethoxybenzene
8.9% of 4-(trans-4-n-propylcyclohexyl)-butoxybenzene
16.3% of 4-(trans-4-n-pentylcyclohexyl)-4'-ethylbiphenyl
7.4% of 4-(trans-4-n-pentylcyclohexyl)-4'-(trans-4-n-propylcyclohexyl)-biphenyl and
26.0% of 2-(4-n-pentylphenyl)-5-n-hexylpyrimidine
has a smectic/nematic phase transition at +24° and a clear point at 63°.

By replacing the last component by the same amount of 2-(3-fluoro-4-n-pentylphenyl)-5-n-hexylpyrimidine, a liquid crystal mixture is obtained which has a nematic phase range from +11° to +53°.

EXAMPLE C

A liquid crystal mixture of
16.7% of 4-(trans-4-ethylcyclohexyl)-benzonitrile
8.3% of 4-(trans-4-n-butylcyclohexyl)-benzonitrile
10.8% of 4-ethyl-4'-cyanobiphenyl
18.3% of 4-n-butyl-4'-cyanobiphenyl
16.7% of 4-(trans-4-n-propylcyclohexyl)-phenyl trans-4-n-butylcyclohexanecarboxylate
12.5% of 4-(trans-4-n-propylcyclohexyl)-phenyl trans-4-n-pentylcyclohexanecarboxylate and
16.7% of 2-(4-n-pentylphenyl)-5-n-hexylpyrimidine
has a smectic/nematic phase transition at −8° and a clear point of 58°. By replacing the last component by the same amount of 2-(3-fluoro-4-n-pentylphenyl)1-5-n-hexylpyrimidine, a liquid crystal mixture is obtained which has a nematic phase range from −18° to +52°.

EXAMPLE D

A liquid crystal mixture of
14.8% of 4-(trans-4-ethylcyclohexyl)-benzonitrile
7.4% of 4-(trans-4-n-butylcyclohexyl)-benzonitrile
9.6% of 4-ethyl-4'-cyanobiphenyl
16.4% of 4-n-butyl-4'-cyanobiphenyl
14.8% of 4-(trans-4-n-propylcyclohexyl)-phenyl trans-4-n-butylcyclohexanecarboxylate
11.1% of 4-(trans-4-n-propylcyclohexyl)-phenyl trans-4-n-pentylcyclohexanecarboxylate and
25.9% of 2-(4-n-pentylphenyl)-5-n-hexylpyrimidine
has a smectic/nematic phase transition at +15° and a clear point of 51°.

By replacing the last component of the same amount of 2-(3-fluoro-4-n-pentylphenyl)-5-n-hexylpyrimidine, a liquid crystal mixture is obtained which has a nematic phase range from +1° to +41°.

EXAMPLE E

A liquid crystal mixture of
12.6% of 4-(trans-5-n-propyl-1,3-dioxan-2-yl)-benzonitrile
17.0% of 4-(trans-5-n-butyl-1,3-dioxan-2-yl)-benzonitrile 10.4% of 4-ethyl-4'-cyanobiphenyl
19.2% of 4-n-butyl-4'-cyanobiphenyl
5.9% of 4-(trans-4-n-pentylcyclohexyl)-4'-cyanobiphenyl
3.7% of 4-cyanophenyl 4-(trans-4-ethylcyclohexyl)-benzoate
5.2% of 4-cyanophenyl 4-(trans-4-n-pentylcyclohexyl)-benzoate and
26.0% of 2-(4-n-pentylphenyl)-5-n-hexylpyrimidine
has a smectic/nematic phase transition at 0° and a clear point of 47°.

By replacing the last component by the same amount of 2-(3-fluoro-4-n-pentylphenyl)-5-n-hexylpyrimidine, a liquid crystal mixture is obtained which has a nematic phase range from −20° to +36°.

EXAMPLE F

A liquid crystal mixture of
11.1% of 4-(trans-4-n-propylcyclohexyl)-benzonitrile
20.0% of 4-(trans-4-n-propylcyclohexyl)-ethylbenzene
7.4% of 4-(trans-4-n-propylcyclohexyl)-ethoxybenzene
5.2% of 4-(trans-4-n-pentylcyclohexyl)-4'-cyanobiphenyl
6.7% of 4-(trans-4-n-propylcyclohexyl)-4'-ethylbiphenyl
5.9% of 4-(trans-4-n-pentylcyclohexyl)-4'-ethylbiphenyl
7.4% of 4-(trans-4-n-pentylcyclohexyl)-4'-(trans-4-n-propylcyclohexyl)-biphenyl
5.9% of 4-n-propylphenyl 4-(trans-4-n-propylcyclohexyl)benzoate
4.4% of 4-n-propylphenyl 4-(trans-4-n-pentylcyclohexyl)benzoate and
26.0% of 2-(4-n-pentylphenyl)-5-n-hexylpyrimidine
has a smectic/nematic phase transition of −17° and a clear point of 58°.

By replacing the last component by the same amount of 2-(3-fluoro-4-n-pentylphenyl)-5-n-hexylpyrimidine, a liquid crystal mixture is obtained which has a nematic phase range from < −20° to +48°.

EXAMPLE G

A liquid crystal mixture of
9% of 4-(trans-5-n-propyl-1,3-dioxan-2-yl)-benzonitrile
12% of 4-(trans-5-n-butyl-1,3-dioxan-2-yl)-benzonitrile
9% of 4-(trans-5-n-pentyl-1,3-dioxan-2-yl)-benzonitrile
6% of 2-(4-n-heptyloxyphenyl)-5-n-hexylpyrimidine
22% of 2-(4-n-octyloxyphenyl)-5-n-hexylpyrimidine
6% of 2-(4-n-nonyloxyphenyl)-5-n-hexylpyrimidine
6% of 2-(4-n-decyloxyphenyl)-5-n-hexylpyrimidine
10% of 4-ethoxyphenyl trans-4-n-propylcyclohexanecarboxylate
10% of 4-ethoxyphenyl trans-4-n-butylcyclohexanecarboxylate and
10% of 4-(trans-4-n-propylcyclohexyl)-4'-ethylbiphenyl
has a melting point of −10°, a clear point of 61° and a smectic/nematic phase transition at +21°.

By replacing 13% of the pyrimidine content of the above mixture by 2-(3-fluoro-4-n-dodecyloxyphenyl)-5-n-hexylpyrimidine, a liquid crystal mixture is obtained which has a melting point of −12°, a clear point of 58° and a smectic/nematic phase transition below −20°. The mixture is distinguished by an advantageous threshold voltage and a steep characteristic line (small $V_{50}/V_{10}$ ratio) and is thus outstandingly suitable for multiplex operation.

EXAMPLE H

A liquid crystal mixture of
14.2% of 4-(trans-4-propylcyclohexyl)-benzonitrile
19.2% of 4-(trans-4-n-pentylcyclohexyl)-benzonitrile
13.3% of 4-(trans-4-n-propylcyclohexyl)-ethoxybenzene
10.0% of 4-(trans-4-n-propylcyclohexyl)-butoxybenzene
18.4% of 4-(trans-4-n-pentylcyclohexyl)-4'-ethylbiphenyl
8.3% of 4-(trans-4-n-pentylcyclohexyl)-4'-(trans-4-n-propylcyclohexyl)-biphenyl and
16.6% of 2-(4-n-pentylphenyl)-5-n-hexylpyrimidine
has a smectic/nematic phase transition at −12° and a clear point of 72°.

By replacing the last component by the same amount of 2-(3-fluor-4-cyanophenyl)-5-n-pentylpyrimidine, a liquid crystal mixture is obtained which has a clear point of 67° and shows no smectic phase down to −30°.

EXAMPLE I

A liquid crystal mixture of
12.6% of 4-(trans-4-propylcyclohexyl)-benzonitrile
17.0% of 4-(trans-4-n-pentylcyclohexyl)-benzonitrile
11.8% of 4-(trans-4-n-propylcyclohexyl)-ethoxybenzene
8.9% of 4-(trans-4-n-propylcyclohexyl)-butoxybenzene
16.3% of 4-(trans-4-n-pentylcyclohexyl)-4'-ethylbiphenyl
7.4% of 4-(trans-4-n-pentylcyclohexyl)-4'-(trans-4-n-propylcyclohexyl)-biphenyl and
26.0% of 2-(4-n-pentylphenyl)-5-n-hexylpyrimidine
has a smectic/nematic phase transition at +24° and a clear point of 63°. By replacing the last component by the same amount of 2-(3-fluor-4-cyanophenyl)-5-n-pentylpyrimidine, a liquid crystal mixture is obtained which has a nematic phase range from < −20° to +65°.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a liquid crystal dielectric useful for electrooptical display elements and comprising at least two liquid crystal components, the improvement wherein at least one component is a fluorine-containing pyrimidine compound of the formula $R^1$—PhF—$R^2$ wherein PhF is 2- or 3-fluoro-1,4-phenylene, one of the radicals $R^1$ and $R^2$ is alkyl of 1 to 12 C atoms and the other is CN and Z is 1,3-pyrimidine-2,5-diyl.

2. A dielectric of claim 1, wherein in said pyrimidine compound the alkyl group is straight-chained.

3. A dielectric of claim 1, wherein said pyrimidine compound is of the formula

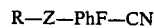

or

wherein R is straight-chained alkyl of 2 to 8 C atoms.

4. A dielectric of claim 1, comprising 2–15 components.

5. In an electrooptical display element comprising a liquid crystalline dielectric, the improvement wherein the dielectric is one of claim 1.

6. A fluorine-containing pyrimidine compound of the formula

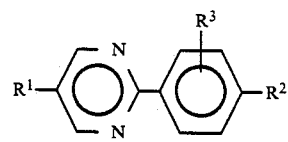

wherein $R^1$ is alkyl of 4 to 12 C atoms, $R^2$ is alkyl or alkoxy of 8 to 12 C atoms, and $R^3$ is fluorine.

7. A compound of claim 6, wherein

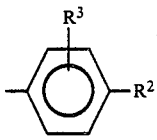

is a 3-fluoro-4-$R^2$-phenyl group.

8. A compound of claim 6, wherein $R^1$ and $R^2$ are straight-chained groups.

9. A compound of claim 8, wherein $R^1$ is n-butyl, n-pentyl, n-hexyl, n-heptyl, n-octyl, n-nonyl, n-decyl, n-undecyl or n-dodecyl.

10. A compound of claim 9, wherein $R^2$ is n-octyl, n-nonyl, n-decyl, n-undecyl, n-dodecyl, n-octyloxy, n-nonyloxy, n-decyloxy, n-undecyloxy or n-dodecyloxy.

11. 2-(3-fluoro-4-n-dodecyloxyphenyl)-5-n-hexylpyrimidine 2-(3-fluoro-4-n-octyloxyphenyl)-5-n-butylpyrimidine
2-(3-fluoro-4-n-octyloxyphenyl)-5-n-pentylpyrimidine
2-(3-fluoro-4-n-octyloxyphenyl)-5-n-hexylpyrimidine
2-(3-fluoro-4-n-octyloxyphenyl)-5-n-heptylpyrimidine
2-(3-fluoro-4-n-octyloxyphenyl)-5-n-octylpyrimidine
2(3-fluoro-4-n-octylphenyl)-5-n-butylpyrimidine
2(3-fluoro-4-n-octylphenyl)-5-n-pentylpyrimidine
2(3-fluoro-4-n-octylphenyl)-5-n-hexylpyrimidine
2(3-fluoro-4-n-octylphenyl)-5-n-heptylpyrimidine
and
2(3-fluoro-4-n-octylphenyl)-5-n-octylpyrimidine,
each a compound of claim 6.

12. In a liquid crystal dielectric useful for electrooptical display elements and comprising at least two liquid crystal components, the improvement wherein at least one component is a compound of claim 6.

13. A dielectric of claim 12, comprising 2-15 components.

14. In an electrooptical display element comprising a liquid crystalline dielectric, the improvement wherein the dielectric is one of claim 12.

* * * * *

UNITED STATES PATENT AND TRADEMARK OFFICE
CERTIFICATE OF CORRECTION

PATENT NO. : 4,812,258

DATED : March 14, 1989

INVENTOR(S) : Krause et al

It is certified that error appears in the above-identified patent and that said Letters Patent is hereby corrected as shown below:

Column 18, Claim 1, Line 38:

Reads: "compound of the formula $R^1$-PhF-$R^2$ wherein PhF is"

should Read: --compound of the formula $R^1$-Z-PhF-$R^2$ wherein PhF is--

Signed and Sealed this

Fourteenth Day of November, 1989

Attest:

JEFFREY M. SAMUELS

*Attesting Officer*     *Acting Commissioner of Patents and Trademarks*